United States Patent
Schwenn et al.

[11] Patent Number: 5,814,001
[45] Date of Patent: Sep. 29, 1998

[54] ORTHOPEDIC HIP AND LEG ABDUCTOR

[75] Inventors: Shannon R. Schwenn, Orland; Bryan J. Puch, Apopka, both of Fla.

[73] Assignee: Orthomerica Products, Inc., Newport Beach, Calif.

[21] Appl. No.: 900,202

[22] Filed: Jul. 25, 1997

[51] Int. Cl.[6] .................................................. A61F 5/00
[52] U.S. Cl. .............................................. 602/24; 602/23
[58] Field of Search ................................... 602/5, 12, 23, 602/24, 16

[56] References Cited

U.S. PATENT DOCUMENTS

| | | | |
|---|---|---|---|
| 3,260,259 | 7/1966 | Connelly | 602/24 |
| 3,815,589 | 6/1974 | Bosley | 602/24 |
| 4,263,901 | 4/1981 | Nichols | 602/24 |
| 4,543,948 | 10/1985 | Phillips et al. | 602/24 X |
| 4,574,790 | 3/1986 | Wellershaus | 602/24 |
| 4,576,151 | 3/1986 | Carmichael et al. | 602/24 |
| 4,691,698 | 9/1987 | Bremer | 602/24 |
| 5,470,310 | 11/1995 | Sutcliffe | 602/24 |
| 5,558,628 | 9/1996 | Bzoch | 602/24 |
| 5,681,270 | 10/1997 | Klearman et al. | 602/24 |

FOREIGN PATENT DOCUMENTS 3508844  9/1986  Germany .................................. 602/24

Primary Examiner—Linda C Dvorak
Attorney, Agent, or Firm—Price, Gess & Ubell

[57] ABSTRACT

An orthopedic leg abductor for resisting muscular contraction of a user comprises a pair of adjustable sleeves which secure about a patient's thighs. The adjustable sleeves are each connected to a separate rigid member, which in turn is connected to a belt which is fastened about the patient's waist. The rigid members preferably comprise a pair of pivoting bars which are lockable in a predetermined angular relationship according to the needs and requirements of the individual patient. The rigid bars give the abductor structure and also serve to prevent the patient from retracting into a fetal position. The sleeves are also separated by mechanical means such as a collapsible hinge which is adjustable to keep the patient's legs apart, thereby reducing the patient's disposition to contract into an undesirable position and provide extension of the muscles in the hip region. The mechanical means fixes the distance between the two sleeves and can be easily locked into position. The apparatus includes covers for each rigid member and mechanical means, and all elements whose surfaces are designed to contact the user are machine washable.

4 Claims, 4 Drawing Sheets

ORTHOPEDIC HIP AND LEG ABDUCTOR

BACKGROUND OF THE INVENTION

1. Field of the Invention

The present invention relates to medical apparatus, and particularly to a device for bracing a user' legs in a predetermined position for the treatment of various muscle atrophying conditions.

2. Description of Related Art

A common affliction among the elderly and the handicapped is a condition in which the body begins to contract into a fetal position during extended periods of extreme inactivity. "Contracture" is a shortening and thickening of the connective tissue fibers which restrict the range of motion of a joint. When a patient is immobilized for extended periods due to sickness or injury, the tissue fibers begin to shorten and contract. A patient in this condition can experience a reduced range of motion in his or her extremities within three days, and trauma, edema, or impaired circulation can accelerate the condition. Contracture can begin as soon as four days after immobilization and clearly observable manifestations can be observed after ten days. After fourteen days, the condition may be so severe as to require surgery to repair. It is estimated that after the fourteenth day of immobilization, it requires ten days of therapy to return he affected extremity to a functional state.

In contracture, the connective tissue of the hips and thighs contract causing the connected muscles to decrease in length. This reduction in muscle length causes the hip, knee, and ankle to flex. The flexure draws the foot and knee toward the body, often against the resistance of a bed surface or restraint. The pressure on the part of the body against the bed can lead to pressure ulcers, a common symptom of patients experiencing contracture. The contracture also occurs with the strong flexion of the hip, causing the patient to curl at the waist. Flexure at the hip will subsequently cause the knees to flex, both as a product of the condition and additionally to reduce the forces at the hip. The contraction at the knees results in the patient assuming a fetal position, of which long term exposure can result in a crippling deformity.

Treatment of contractures in the past has been attempted with splinting devices, which straighten the legs using a plastic shell with a reusable, washable liner. However, patients with the condition often times cannot straighten their legs and find it difficult to keep their hips from flexing even with their legs straightened.

SUMMARY OF THE INVENTION

The present invention is a hip and leg abductor which supports a patient's pelvis, and positions the patient's hips and legs in a plurality of positions. A sturdy belt is placed around the patient's waist and secured using any suitable method. The belt is sufficiently stiff to provide pelvic support, and mount hip joints comprising a first pair of rigid bars mounted at a first end to the belt. A second pair of bars are pivotally connected to the first pair of bars, and the connected bars include a locking mechanism for securing the hip joint in a plurality of angular positions. The second pair of bars are each connected to a sleeve designed to retain the patient's thighs such that the relative position of the lower bars determine the angular position of the patient's thighs and torso. The abductor also includes a mechanical means to adjustably separate the patient's thighs by a pre-selected distance. In a preferred embodiment, a pair of scissoring members pivoting about a pin provide the mechanical means to separate the patient's legs, including locking means for securing the members in a selected position.

BRIEF DESCRIPTION OF THE DRAWINGS

The exact nature of this invention, as well as its objects and advantages, will become readily apparent upon reference to the following detailed description when considered in conjunction with the accompanying drawing, wherein.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a hip and thigh abductor with adjustable positions.

Figure 2:
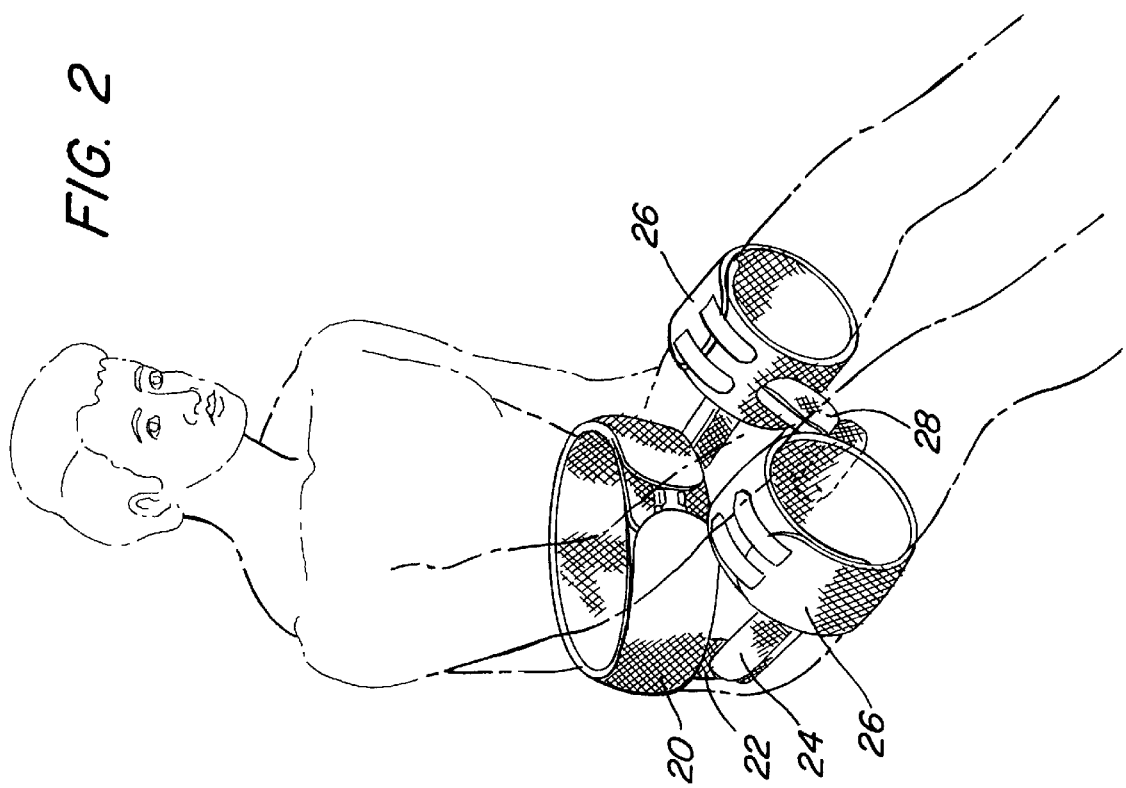
FIG. 2 is an elevated perspective view of the present invention worn by a patient in an extended position.
Figure 1:
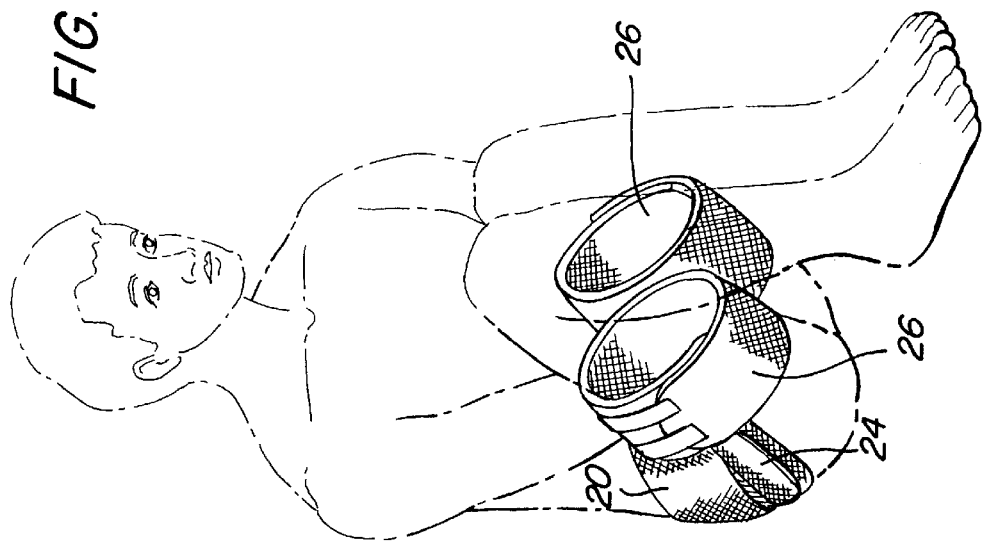
FIG. 1 is an elevated perspective view of the present invention worn by a patient in a contracted position.

FIGS. 1 and 2 generally illustrate a preferred embodiment of the present invention as worn by a patient. A belt 20 secured around the patient's waste has depending from it two rigid members 22 located generally at the patient's left and right hips. Connected to the rigid members 22 are pivoting lower rigid members 24 that are connected at an end to a thigh sleeve 26. Each thigh sleeve 26 in turn is connected to a collapsible hinge assembly 28 for expanding and contracting the space between the two thigh sleeves 26. As can be seen from FIGS. 1 and 2, a variety of positions are possible to accommodate the particular needs of the patient by varying the angle of pivot between the first rigid member 22 and lower rigid member 24, and by adjusting the collapsible hinge assembly 28 as will be explained more fully below.

Figure 3:
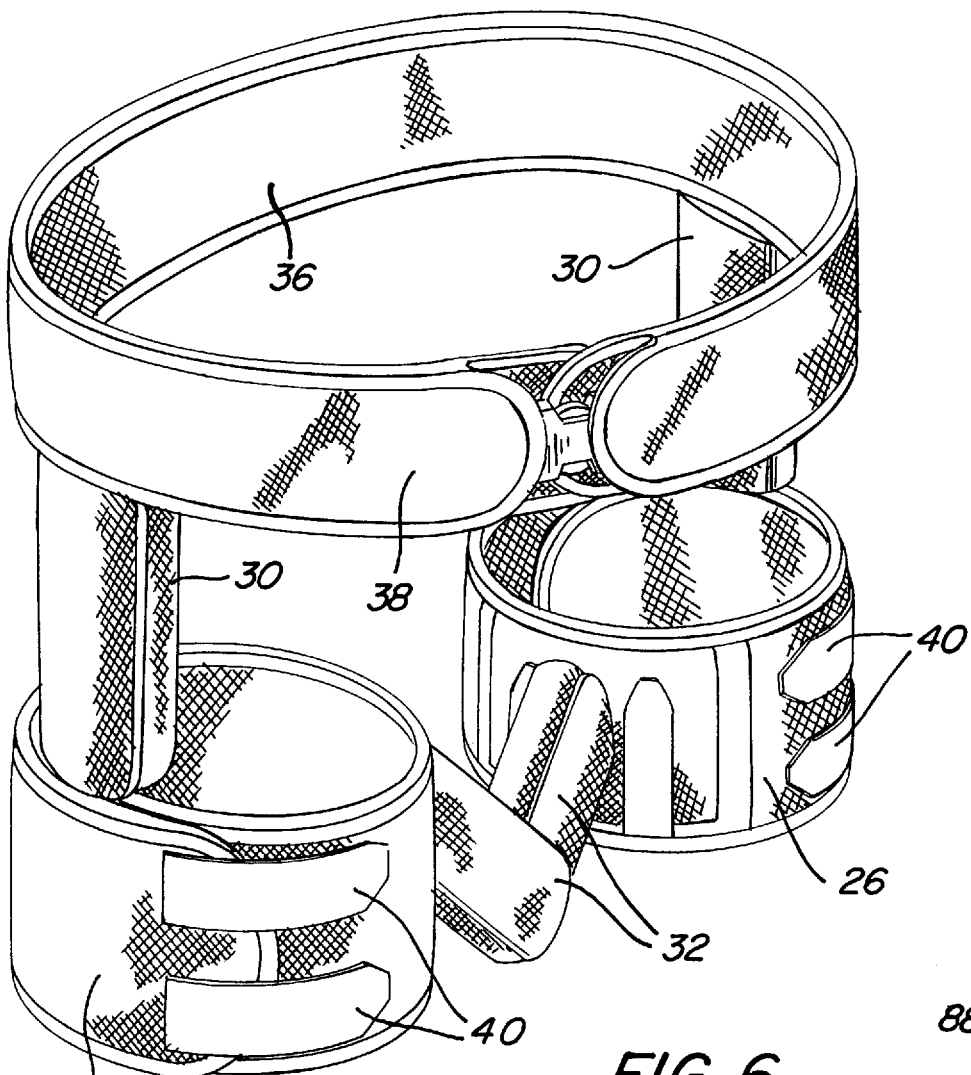
FIG. 3 is an elevated perspective view of the present invention with protective coverings.

FIG. 3 illustrates a preferred embodiment of the present invention including protective coverings for all of the moving elements of the apparatus to prevent pinching the patient's skin and for greater comfort when wearing the apparatus. An important advantage of the present invention is that each of the protective coverings are removable and washable. A flexible padded wrap 30 or other protective sheath is placed around the linkages at the sides of the apparatus, and the collapsible hinge assembly is protected by a similar pad 32 or wrap. In a preferred embodiment, Velcro® pressure sensitive hooks and loops are used to secure the coverings because of the ease of use and the lack of removable parts. Other embodiments could include the use of snaps, buckles, or the like. Similarly, the collapsible hinge assembly 28 is covered by wraps 32 to guard against pinching or cutting the patient. The wraps 30,32 are removable and washable, features which are often convenient to those in charge of caring for the disabled and elderly.

Also shown in FIG. 3 is a protective jacket 34 for the belt 20. The protective jacket 34 comprises a soft padded material having a first inner layer 36 which folds over into a second outer layer 38. The jacket 34 preferably includes cooperating Velcro® hooks and loops which releasably secure the belt in between the two layers, although other means of securing the layers together may be envisioned. The belt 20 is preferably a two piece belt which overlaps to adjust circumferentially to different sized patients, and connects using Velcro® hooks and loops in the back. The belt 20 is secured between folds 36 and 38 of the jacket 34 to insulate the patient from contact with the belt, which may have pointed edges or rough surfaces.

Also shown in FIG. 3 are the thigh sleeves 26, which are preferably comprised of a softer, padded material on the inside and a durable material on the outside. The thigh sleeves 26 are preferably formed from an elongated length of material that is wrapped around the thighs until a firm but comfortable fit is achieved, and then secured at the loose end to the outer surface of the thigh sleeve 26. Straps 40 having Velcro® patches are used to adjustably secure the thigh sleeves 26 to different sized legs comfortably, although again buckles or other fastening methods are possible.

Figure 4:
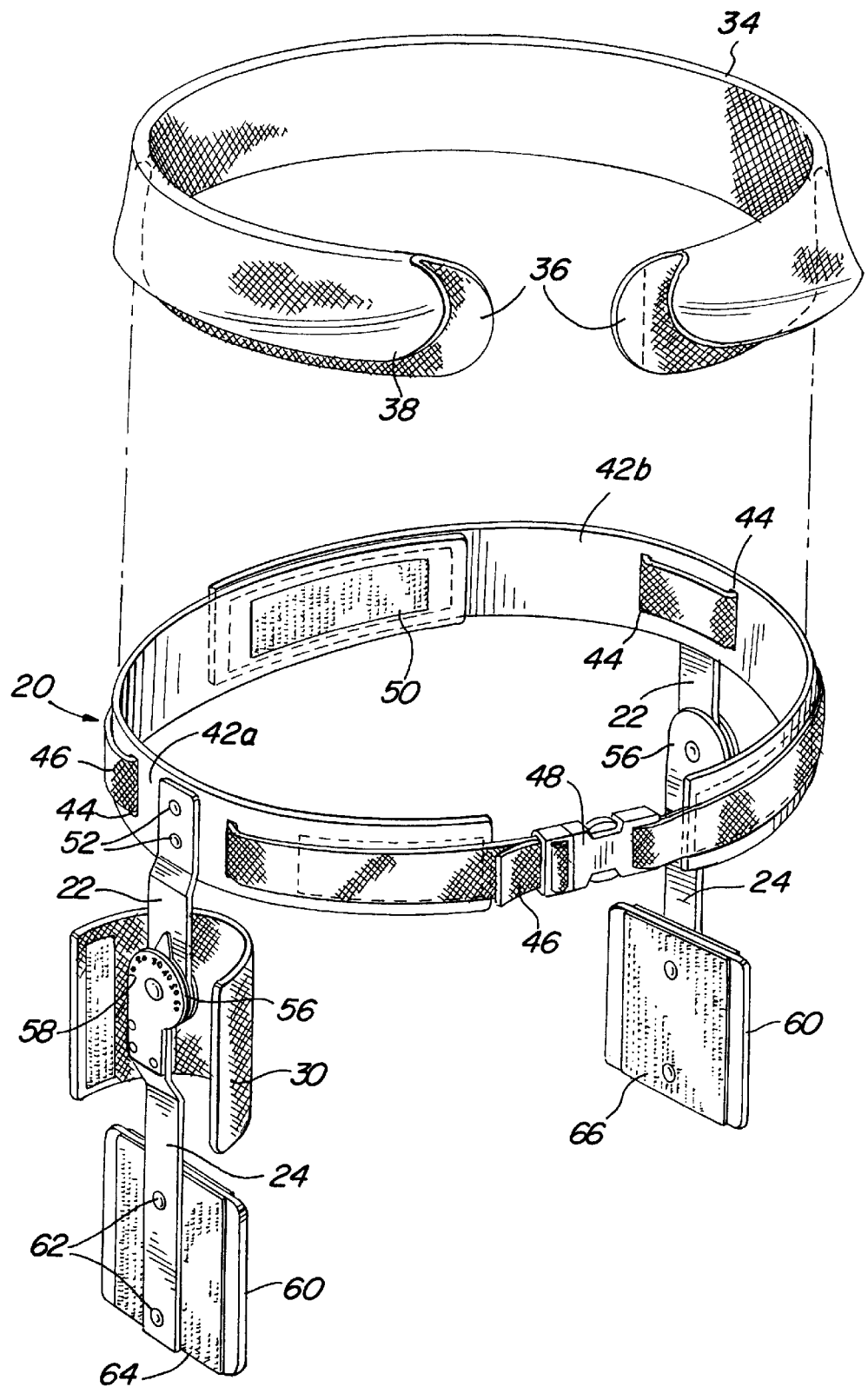
FIG. 4 is a partially exploded view of the present invention with protective coverings removed.

Turning to FIG. 4, the abductor will now be described. A belt 20 is comprised of a pair of flexible bands 42a,b which overlap and connect at the rear of the patient using Velcro® or other fastening means. The bands 42a,b are preferably of a plastic material have some rigidity, especially in the transverse direction. That is, the belt easily flexes longitudinally so as to follow the contour of a patient's waist but resists bending laterally to provide adequate support for the connected bars. The rigidity in the belt provides pelvic support for the patient and aids in the precision with which the hip joints may be positioned. The flexible bands 42a,b include slits 44 through which a strap 46 passes. The strap 46 encircles the bands 42a,b and includes a buckle 48 at the end for securing the belt 20 to the patient's waist. The bands 42a,b include at spaced intervals patches of Velcro® 50 which are used to secure the jacket 34 onto the belt 20. As can be seen in FIG. 4, the jacket 34 slips over the belt 20 and attaches to the belt at Velcro® patches 50.

Riveted to the belt 20 at opposite sides are a pair of hip joints comprising a first pair of rigid bars 22 and a second pair of rigid members 24, located generally at the patient's left and right hips. A pair of holes 52 are provided through which rivets or other fasteners are passed to connect the bars 22 to the belt 20. The bars 22 are pivotally connected to lower members 24 at a pin 54, which allows the lower bar 24 to rotate about the end of the upper bar 22. The pivoting connection 56 preferably is of a type such as U.S. Pat. No. 5,460,599 by Davis et al., incorporated by reference herein, but may be any pivoting connection which is lockable in a selected angular position. Moreover, indicia 58 is preferably located on the pivoting connection 56 to more accurately measure the angular position and to monitor changes in the patient's range of motion.

The lower bar 24 is rigidly connected to a paddle 60 using fasteners 62. The paddle 60 may be formed of a plastic material and include Velcro® sheets 64,66 on the outer and inner surfaces, respectively. The paddle 60 is attached to the thigh sleeve 26 after the thigh sleeve has been partially wrapped around the patient's thigh, with the sleeve continuing to wrap around the paddle 60 in subsequent revolutions to enclose the paddle within the thigh sleeve. The Velcro® sheets 64,66 on the inner and outer surfaces of the paddle 60 attach to the thigh sleeve to provide a sturdy connection between the two components.

Figure 5:
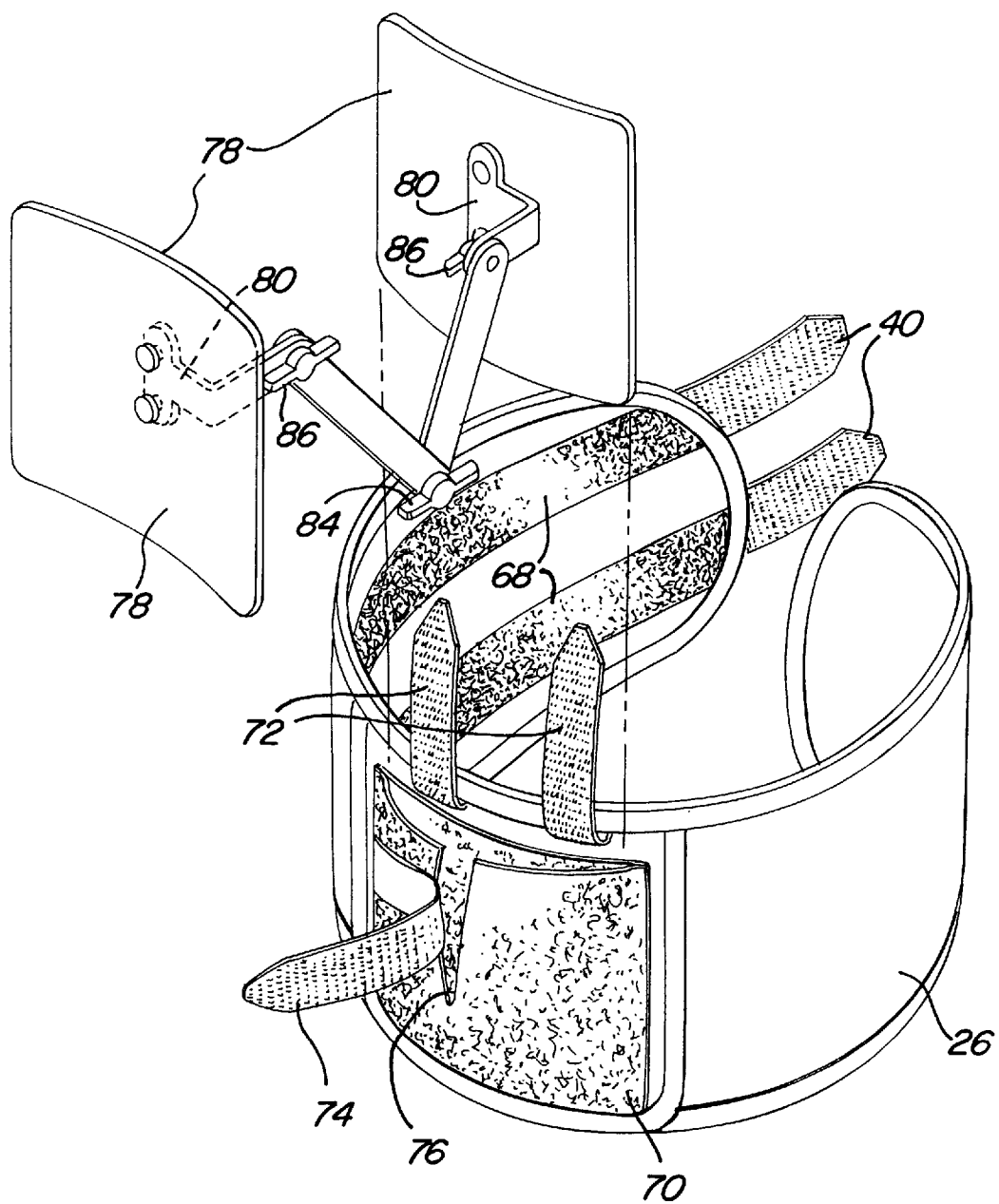
FIG. 5 is an elevated perspective view of the thigh paddles and abductor bar arrangement.

The collapsible hinge assembly 28 connecting the two thigh sleeves will now be described with reference to FIG. 5. Thigh sleeve 26 wraps around the patient's thigh and straps 40 with Velcro fasten the sleeve tight by attaching to he outer surface of the thigh sleeve. Velcro strips 68 on the inner surface of the high sleeve assist in the adjustment of the sleeve. On the outside surface of the thigh sleeve 26 at the inner thigh position is a Velcro® pocket 70 which is accessed by opening Velcro® straps 72 and 74. The straps 40 are preferably long enough to secure to the pocket 70, although other locations are possible. Pocket 70 has a slit 76 in an outer layer which provides access to the interior of the pocket 70. The pocket 70 is sized to receive a plate 78 inside, upon which an L-shaped bracket 80 is mounted. With the plate 78 in the pocket 70, the slit 76 permits the L-shaped bracket 80 to extend out of the pocket, and the straps are positioned to secure the plate inside the pocket.

To adjust the distance between the patient's thighs, the plates 78 positioned on the inner portion of the patient's thighs and the connected brackets 80 are pivotally connected to bars 82, which in turn are connected together by the pin 84. The motion of the bars 82 pivoting at the brackets 80 and the pin 84 cause the collapsible hinge assembly to expand and contract. The pin 84, as well as pins 86 connecting the bars 82 to the brackets 80, are each lockable using wing nuts or other locking means to set the collapsible hinge assembly in the desired spaced apart relationship. The configuration allows the patient's legs to be positioned with some specificity, which can be adjusted or measured as time passes. Other configurations are possible which expand and contract the thigh sleeves 26 in a releasably locked position without deviating from the scope of the present invention.

Figure 6:
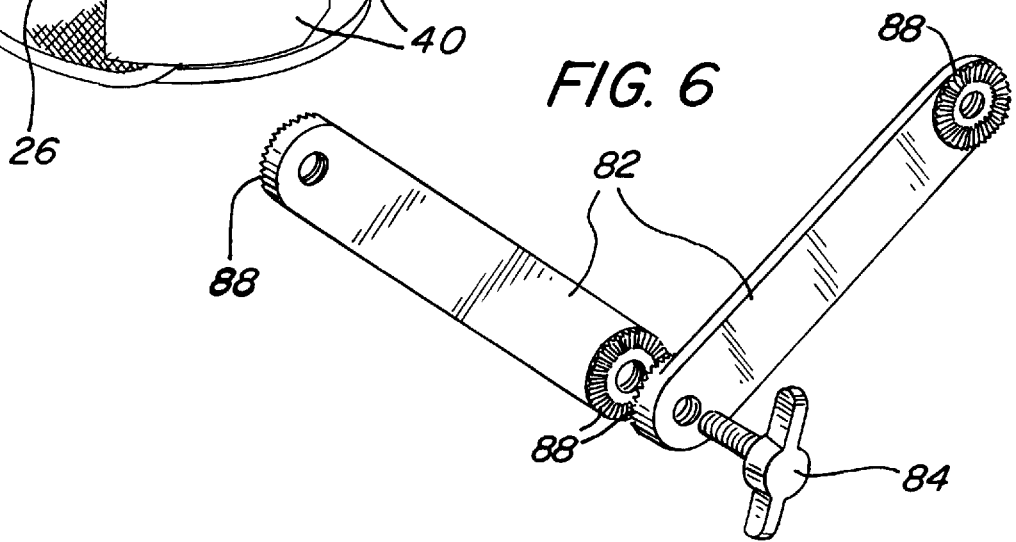
FIG. 6 is a view of a preferred embodiment of the pinned joints of the collapsible hinge.

FIG. 6 illustrates a preferred embodiment of the pinned joints of the collapsible hinge assembly. Each mating bar 82 includes a hole through which a pin 84 is inserted, and a locking nut (not shown) may be used to secure the assembly. To assist in the locking capability of the joint, each contact surface 88 is provided with a corrugated region which mates with a similar corrugated region to resist slipping at the joint. When placed in contact with each other, the contact surfaces 88 resist relative rotation due to the mating of the corrugated regions such that slip between the bars 82 is minimized. Other surfaces, such as a sand paper-like texture or other frictional enhancing surface can be used to resist slipping once the joint is tightened.

It will be understood that the embodiment described herein are merely exemplary and that a person skilled in the art may make many variations and modifications without departing from the spirit and scope of the invention. All such variations and modifications are intended to be included within the scope of the invention as defined in the appended claims.

What is claimed is:

1. An orthopedic leg abductor comprising:

a belt to be secured about a user's torso;

first and second adjustable thigh sleeves, and first and second plates mounted so as to be opposed to each other on said first and second adjustable thigh sleeves;

a pair of locking linkages each comprising first and second rigid members connected in a pivoting relationship, each linkage connecting said belt to one of said adjustable sleeves, said linkage determining an angular relationship between said belt and said connected adjustable sleeve, said linkages further including a rigid paddle for insertion into said connected adjustable sleeve; and a collapsible hinge assembly separating said first and second plates of said adjustable thigh sleeves, said collapsible hinge assembly determining an expandable distance between said first and second adjustable thigh sleeves.

2. The orthopedic leg abductor of claim 1 further comprising removable protective sheath wrapped around the linkages.

3. The orthopedic leg abductor of claim 1 wherein said belt comprises a pair of overlapping flexible bands cooperating to expand and contract the belt, a strap passing through said flexible bands, and a protective jacket about said pair of overlapping flexible bands.

4. The orthopedic leg abductor of claim 1 wherein said plates on said thigh sleeves include an L-shaped bracket, said L-shaped bracket providing a point of connection for said collapsible hinge assembly, and said collapsible hinge assembly including mating corrugated surfaces at a pivoting point for resisting slippage between the surfaces thereby establishing a fixed position between said thigh sleeves.

* * * * *